US00PP13027P2

(12) United States Plant Patent
van Holsteijn

(10) Patent No.: US PP13,027 P2
(45) Date of Patent: Oct. 1, 2002

(54) GERANIUM PLANT NAMED 'BONITO'

(75) Inventor: Cornelis Joannes Clemens van Holsteijn, Honselersdijk (NL)

(73) Assignee: Florfis Ag, Binningen (CH)

( * ) Notice: Subject to any disclaimer, the term of this patent is extended or adjusted under 35 U.S.C. 154(b) by 41 days.

(21) Appl. No.: 09/657,545

(22) Filed: Sep. 8, 2000

(51) Int. Cl.[7] ..... A01H 5/00
(52) U.S. Cl. ..... Plt./325

(58) Field of Search ..... Plt./325

*Primary Examiner*—Bruce R. Campell
*Assistant Examiner*—Anne Marie Grünberg
(74) *Attorney, Agent, or Firm*—Foley & Lardner

(57) ABSTRACT

Geranium 'Bonito' is a new and distinct cultivar of geranium plant, particularly characterized by the combined features of dark-purple, white edged, double flowers, small, semi-spherical umbels, deep green, zoned foliage, weak growth with moderate branching, resulting in medium tall, somewhat open plant habit, and medium to late spring flowering response.

1 Drawing Sheet

BACKGROUND OF THE INVENTION

The present invention comprises a new and distinct cultivar of geranium, botanically known as *Pelargonium peltatum*, and hereinafter referred to by the cultivar name 'Bonito'.

'Bonito' originated from a naturally occurring mutation in the variety 'Barbe Blue' that was discovered by C. van Holsteijn in a greenhouse in Honselersdijk, Netherlands, in May 1994.

An apparently completely mutated plant developing white bordered flowers was discovered among a group of flowering pot plants of the parent variety. The parent variety 'Barbe Blue' was characterized by deep purple flower color, small, relatively dark green foliage, and compact growth habit.

Shoot tips of the mutated plant were taken for propagation by the inventor in Honselersdijk during the summer of 1994. The resulting plants were carefully examined for deviations, and proved to be uniform for the new characteristic.

Horticultural examination of plants grown from the plant initiated in the spring of 1998 in Hillscheid, Germany, and continuing thereafter, has demonstrated that the combination of characteristics as herein disclosed for 'Bonito' are firmly fixed and are retained through successive generations of asexual reproduction.

BRIEF DESCRIPTION OF THE DRAWINGS

The accompanying photographic drawing shows typical flower and foliage characteristics of 'Bonito' with colors being as true as possible with illustrations of this type. The photograph is a close view of a flowering branch with flowers, buds, and leaves.

The measurements were taken in Langley, Canada, on Jun. 15, 1999, 12 weeks after planting of rooted cuttings into 15 cm pots. The plants had not been pinched.

In the following description color references are made to The Royal Horticultural Society Colour Chart. The color values were determined indoors from flowers developed in a greenhouse in May 1999 in Hillscheid, Germany.

BRIEF SUMMARY OF THE INVENTION

The following traits have been repeatedly observed and are determined to be basic characteristics of 'Bonito', which in combination distinguish this geranium as a new and distinct cultivar:

1. Deep purple colored and white-bordered, double flowers;

2. Small, semi-spherically shaped inflorescence;

3. Small, relatively dark green colored leaves with distinct zonation;

4. Mid season to late flowering;

5. Relatively weak growth and moderate branching ability;

6. Medium tall, somewhat open and slightly trailing plant habit; and

7. Suitable especially for mixed planting in tubs and hanging-baskets.

Of the many commercial cultivars known to the present inventor, the most similar in comparison to 'Bonito' are the parental variety 'Barbe Blue' and the unpatented variety 'Mexicana', synonym 'Rouletta'.

In comparison to 'Barbe Blue', 'Bonito' has flowers with variegated petals and with a slightly lighter ground color. Furthermore, growth is somewhat more vigorous while other characteristics are fairly close to 'Barbe Blue'.

In comparison to 'Mexicana', 'Bonito' has dark purple flowers with black markings on the upper petals whereas 'Mexicana' has red-purple flowers, RHS 57C, without the black markings. 'Bonito' has medium size flowers whereas 'Mexicana' has medium to large size flowers with a diameter of more than 50 mm. The peduncles of 'Mexicana' are almost twice as long as those of 'Bonito'. Lastly, 'Bonito' is a relatively compact plant with short internodes while 'Mexicana' exhibits vigorous growth, trailing plant habit with long branches and long internodes.

'Bonito' has not been observed under all possible environmental conditions. The phenotype may vary significantly with variations in environment such as temperature, light intensity and day length.

DETAILED BOTANICAL DESCRIPTION

The following observations, measurements, and comparisons describe plants grown in Hillscheid, Germany, and in Langley, British Columbia, Canada, under greenhouse conditions which approximate those generally used in commercial practice.

CLASSIFICATION

Botanical: A hybrid of the species *Pelargonium peltatum* L'Héritier.

Commercial: Ivy-leafed geranium, cv. 'BONITO'.

INFLORESCENCE

Umbel:

*Shape.*—Almost semi-spherical.

*Average diameter.*—69 mm.

*Average depth.*—42 mm.

*Peduncle length.*—79 mm.

*Peduncle color.*—Green, color range from RHS 143 B to RHS 143 C.

*Pedicel.*—25 mm long, with spur.

*Pedicel color.*—Mainly green, RHS 143 B, dull dark red stripe on one side, RHS 185 B.

*Number of flowers per umbel.*—About 6–9.

Corolla:

*Average diameter.*—44 mm.

*Form.*—Double.

*Shape.*—Small, nearly round, with arrow petals.

*Number of petals.*—15.3 on average.

*Number of petaloids.*—1–2.

*Color (general tonality from a distance of three meters).*—Dark purple with white margin.

*Color of upper petals.*—Blackish purple, color range from RHS 187 A to RHS 187 B.

*Markings of upper petals.*—Two black veins at the base.

*Color of lower petals.*—Red purple, color range from RHS 60 A to RHS 61 A.

*Color of margin of petals.*—White to very light violet, color range from RHS 75 C to RHS 75 D.

*Color of lower surface of petals.*—RHS 74 B, with distinct black veins.

*Color of sepals.*—Mainly green, RHS 143 B, partly reddish-brownish infused near the base, RHS 179 B.

*Number of sepals.*—5.

Bud: (immediately before unfolding of the petals):

*Shape.*—Elliptical.

*Color (adaxial=sepals).*—Green, near RHS 137 C.

*Color (abaxial=petals).*—Violet-pink, RHS 74 B or lighter.

*Length.*—15 mm.

*Width.*—12 mm.

Reproductive organs:

*Androecium.*—5–7 fertile stamens, yellow-orange pollen, RHS 30 A, filaments whitish, RHS 155 D to light pink, RHS 68 D, black lower side of open anthers, RHS 187 A.

*Gynoecium.*—5–6 lobed stigma, violet RHS 74 A, pistil whitish RHS 56 D to pink, RHS 68 D.

*Fertility/seed set.*—No seed set observed.

Spring flowering response period: In Hillscheid, Germany, in 1999 plants had on average 0.2 flowers opened 12 weeks after planting of unrooted cuttings (pinched plants).

Outdoor flower production: Moderately floriferous, but steady flowering throughout the summer, the flower count in Hillscheid, Germany, in 1999 indicated 1–2 inflorescence per plant in mid May.

Durability: Good shatter resistance, fair rain resistance for a double flowered variety, good stability of flower color (little fading).

PLANT

Foliage: Form ivy-shaped, with distinct lobes, partly overlapping base, and with glossy surface.

*Margin.*—Entire.

*Size of leaf.*—73 mm wide.

*Color of upper surface.*—Dark-green, approximately RHS 137 B.

*Color of zonation.*—Brown, about RHS 166 A.

*Tolerance of botrytis.*—Relatively good, due to the smooth, glossy surface.

General appearance and form:

*Internode length.*—20–30 mm.

*Branching pattern.*—5.8 branches.

*Size of plant/length of branches.*—22.5 cm (12 weeks after planting). 60–80 cm (in early September, 30 weeks after planting).

I claim:

1. A new and distinct cultivar of geranium plant named 'Bonito', as described and illustrated.

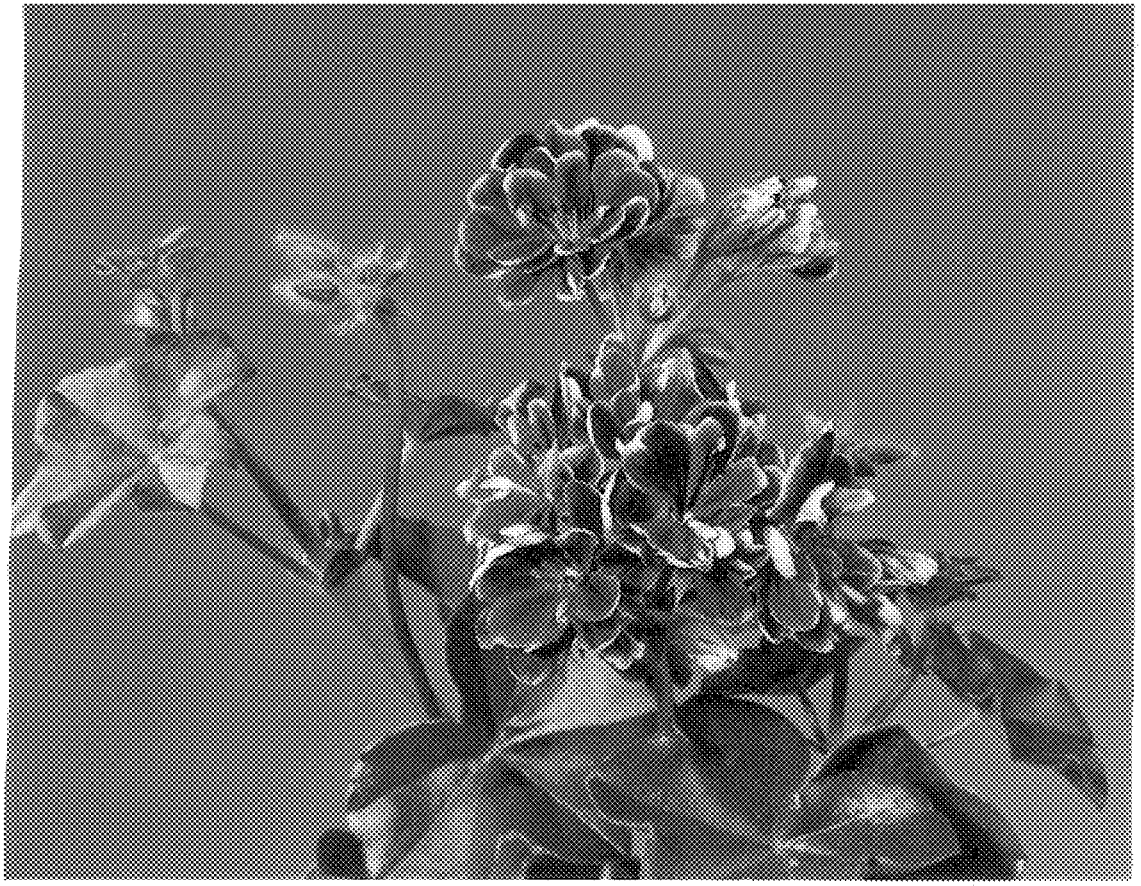

* * * * *